United States Patent [19]

Kaish

[11] Patent Number: 5,501,231
[45] Date of Patent: Mar. 26, 1996

[54] PATIENT OPERATED SYSTEM FOR TESTING AND RECORDING A BIOLOGICAL CONDITION OF THE PATIENT

[76] Inventor: Norman Kaish, 7-24 166th St., Whitestone, N.Y. 11357

[21] Appl. No.: 71,164

[22] Filed: Jun. 2, 1993

[51] Int. Cl.$^6$ .................................................. A61B 5/087
[52] U.S. Cl. ............................ 128/725; 128/671; 73/23.3
[58] Field of Search ........................... 128/725, 716, 128/719, 720, 724, 726, 727, 728, 670, 671, 656, 731, 733, 734, 902; 73/23.3

[56] References Cited

U.S. PATENT DOCUMENTS

| | | | |
|---|---|---|---|
| 4,250,890 | 2/1981 | Jones et al. | 128/728 |
| 4,296,756 | 10/1981 | Dunning et al. | 128/725 |
| 4,635,647 | 1/1987 | Choksi | 128/728 |
| 5,211,180 | 5/1993 | Wright et al. | 128/725 |

Primary Examiner—Lee S. Cohen
Assistant Examiner—Brian M. Green

[57] ABSTRACT

A method and system for testing and recording the peak expiratory flow rate (PEFR), forced expiratory volume (FEV. 1) and forced volume capacity (FVC) of a patient, comprises prompting the patient to cause the sensing of the expiratory flow rate, sensing the expiratory flow rate of the patient and generating a signal representative of this biological condition, processing the signal to generate biological data representative of the biological condition, generating time data representative of the time when the biological condition was sensed, storing the biological data and the time data, and retrieving the stored biological data together with the time data.

55 Claims, 10 Drawing Sheets

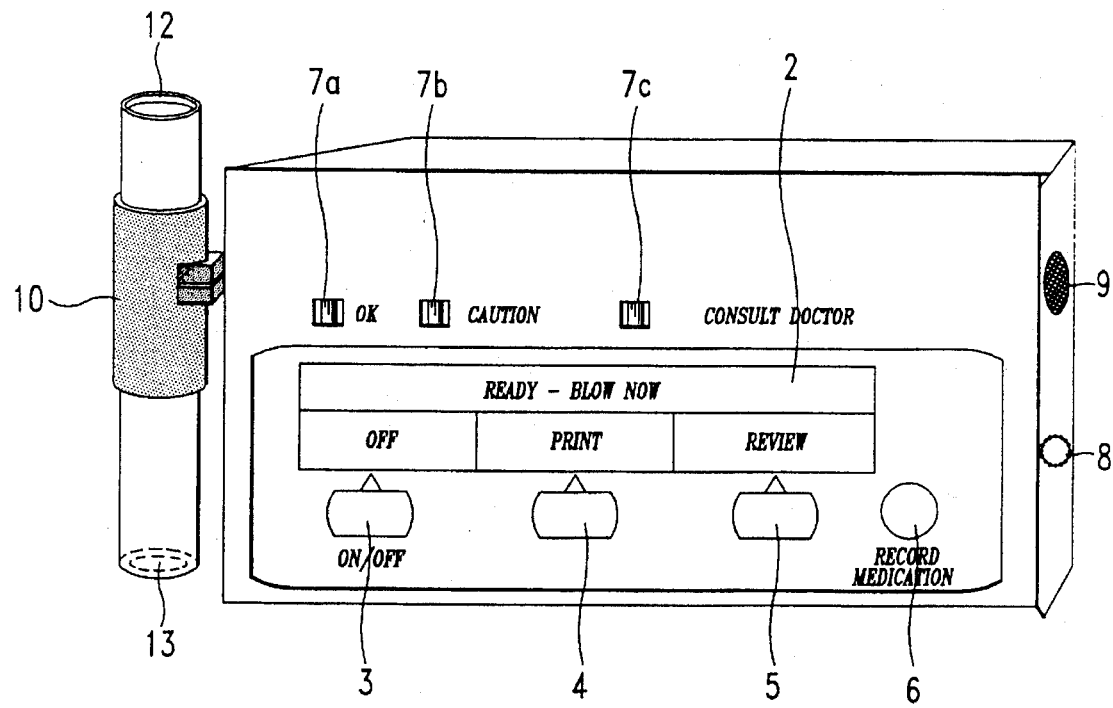
FIG. 1
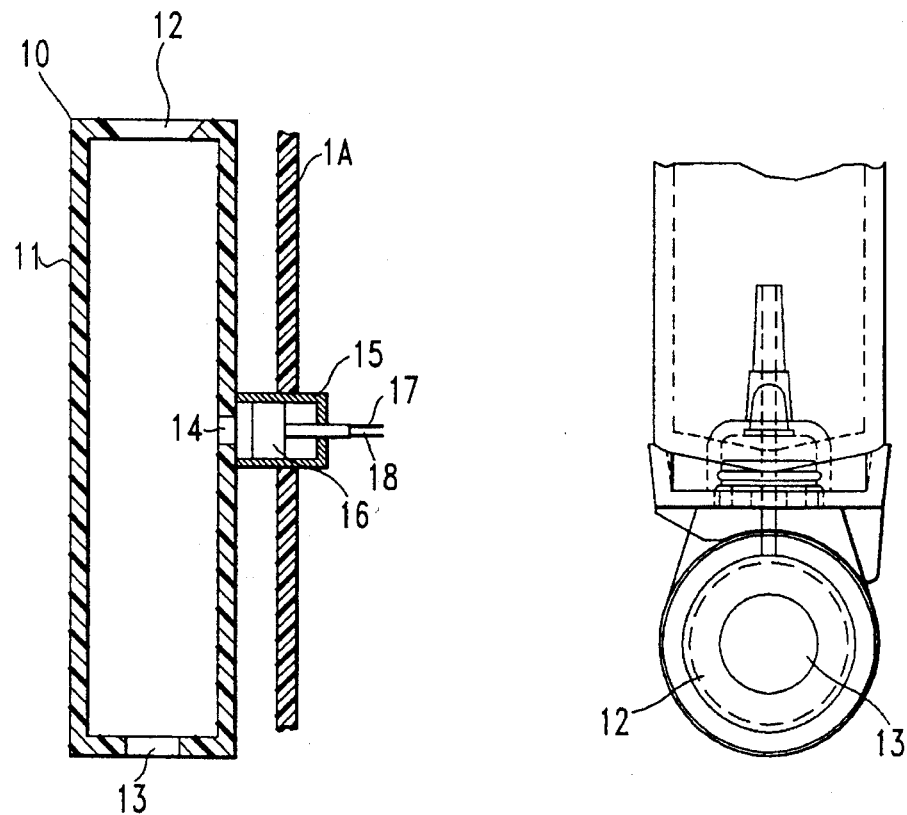
FIG. 2
FIG. 3

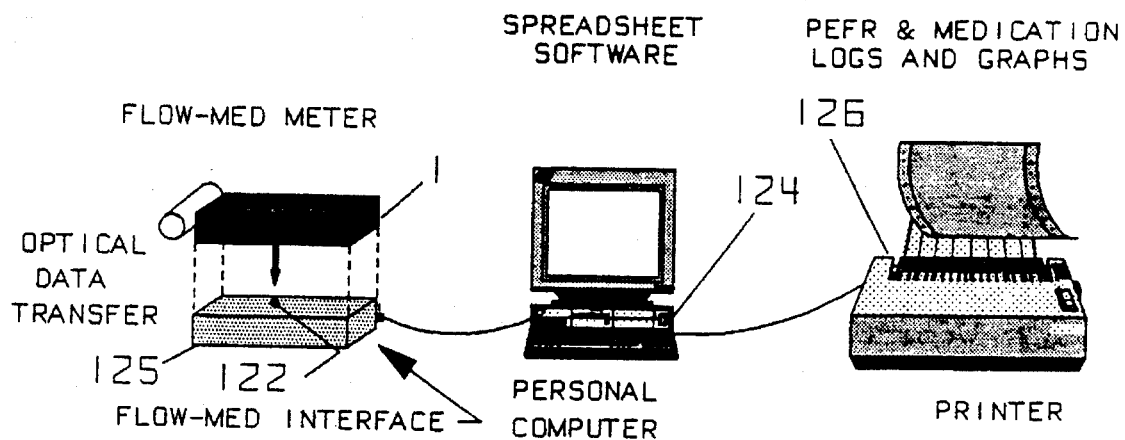
FIGURE 6
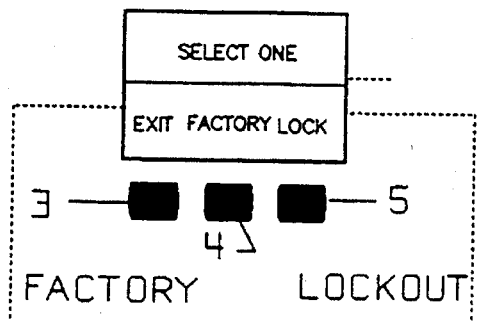
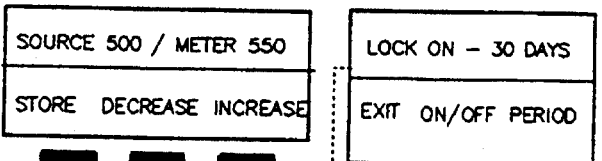
FIGURE 7
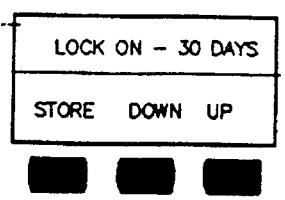

PATIENT OPERATED SYSTEM FOR TESTING AND RECORDING A BIOLOGICAL CONDITION OF THE PATIENT

BACKGROUND OF THE INVENTION

The present invention is directed to a patient operated instrument and method for testing and recording a biological condition of the patient, and more specifically to a system which measures the forced peak expiratory flow of air expelled by the patient when blowing into a measuring tube, as well as other respiratory functions.

Devices of this type are known as peak flow meters, which measure the peak expiratory flow rate (PEFR) that occurs during the first few hundred milliliters of volume expired, when a maximum exhalation is carried out forcibly from total lung capacity. Other devices are known which measure forced expiratory volume in the first second (FEV 1) and forced vital capacity (FVC). These procedures are patient dependent with regard to effort and volume.

According to the National Institute of Health National Asthma Education program's statement on the technical standards for peak flow meters, released in February 1991, if properly utilized, measurement of PEFR serves as a valuable adjunct to patient care.

Numerous products exist that have the capability to measure PEFR, FEV. 1 and FVC. However, most peak flow meters in particular are mechanical devices that lack calibration capability and all require the patient to manually record the data derived from the peak flow test. A major disadvantage of these prior art devices is the lack of patient compliance with diligent manual recording, as well as the lack of accurate and objective recording of test results.

Moreover, while most peak flow meters are accurate in the mid-range, errors in the high or low ranges are not uncommon. Additionally, temperature and humidity are not compensated for in these units and the wearing out of mechanical parts causes significant errors in some if not all devices over the course of time.

Another problem that exists with regard to prior art peak flow meters is that the patient is expected to remember to take tests at specific times during the course of each day, take the prescribed medications after each test, evaluate the performance of the medication by repeating the test several minutes later and then record the results. It is no wonder that the problem of non-compliance is particularly prevalent for devices of this type.

SUMMARY OF THE INVENTION

The main object of the present invention is to overcome the disadvantages of the prior art devices and methods.

Another object of the present invention is to provide a system which obviates the need for the patient to manually record the results of the tests.

Still another object of the present invention is to provide a system which reduces patient non-compliance by prompting the patient to take PEFR tests and medication at predetermined desired time intervals and automatically logging the test data together with time data when the tests are taken.

Still another object of the present invention is to provide a peak flow meter which is also capable of measuring FEV. 1 and FVC.

These and other objects and advantages of the present invention are achieved in accordance with the present invention by a patient-operated instrument for monitoring and recording the forced peak expiratory flow rate of air of the patient which comprises a portable housing, prompter means in the housing for prompting the patient to operate the instrument, a sensor affixed to the housing for sensing the expiratory flow rate of air of the patient and for generating a signal representative of this biological condition, a processor in the housing for processing the aforementioned signal to generate biological data representative of the flow rate of air, a timing device in the housing for generating time data representative of the time when the flow rate of air was sensed, a storage device in the housing for storing the biological data produced by the processor means and the time data produced by the timing device and a retrieval device in the housing for retrieving from the storage means, the biological data together with the time data.

The present invention is also achieved by a method for monitoring and recording the forced peak expiratory flow rate of air of the patient, comprising the steps of prompting the patient to cause the sensing of the flow rate of air; sensing the flow rate of air of the patient and generating a signal representative of this flow rate of air; processing the signal to generate biological data representative of the flow rate of air; generating time data representative of the time when the flow rate of air was sensed; storing the biological data and the time data; and retrieving the stored biological data together with the time data.

For a full understanding of the present invention, reference should now be made to the following detailed description of the preferred embodiments of the invention as illustrated in the accompanying drawings.

BRIEF DESCRIPTION OF THE DRAWINGS

FIG. 1 is a plan view of a PEFR testing device according to the present invention.

FIG. 2 is a representational side view of the measuring tube of FIG. 1.

FIG. 3 is a cross-sectional top view of the measuring tube of FIG. 1.

FIG. 6 is a block diagram illustrating an entire system of which the device of FIG. 1 is a part.

FIG. 7 is a menu diagram illustrating the factory calibrate and patient lock-out menu for the device of FIG. 1.

DESCRIPTION OF THE PREFERRED EMBODIMENTS

Figure 4:
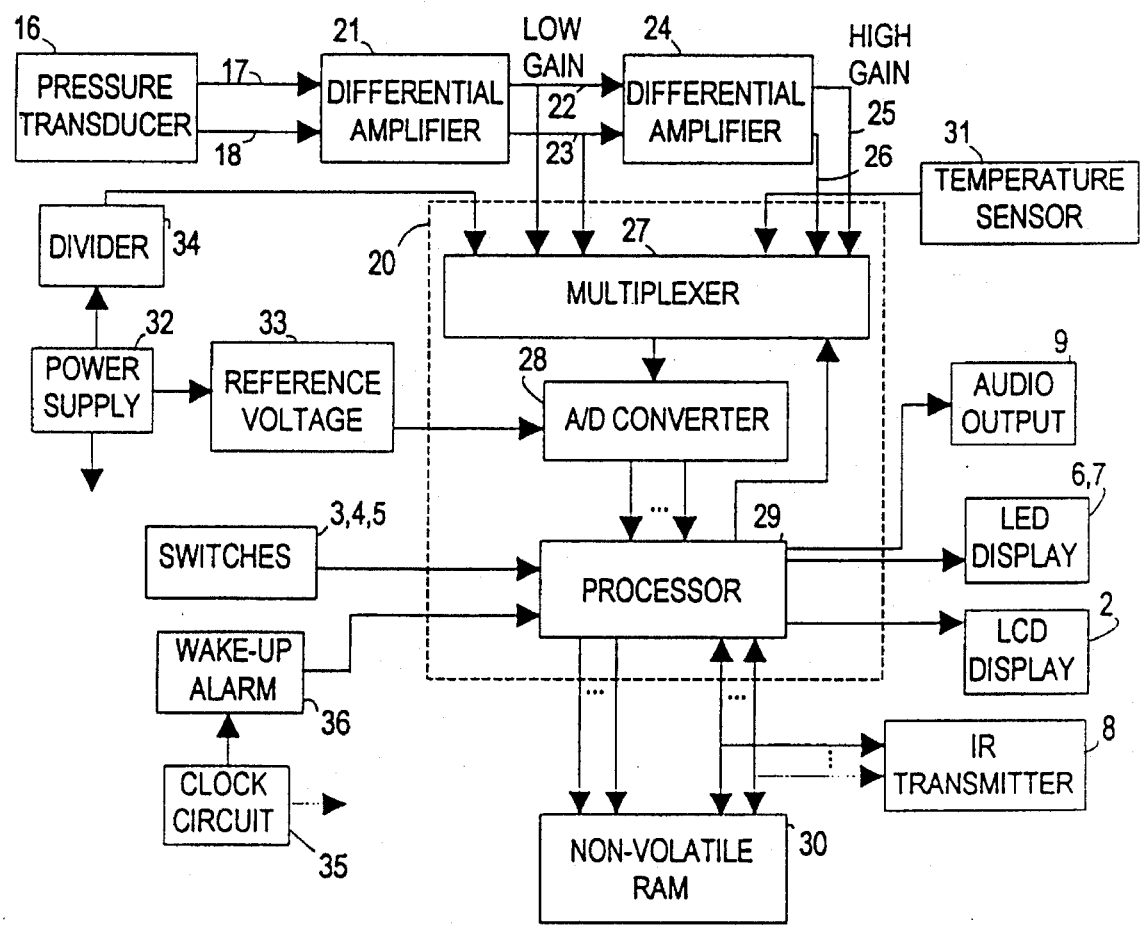
FIG. 4 is a block diagram of the circuit of the device of FIG. 1.

Referring to FIG. 1, the PEFR instrument or device according to the invention, is configured in a palm size portable housing 1 to which a breathing tube assembly 10 is removably attached. The breathing tube assembly is shown in more detail in FIG. 2.

The device includes an LCD display 2, four pushbutton switches 3–6 and LED displays 7a, 7b, and 7c. The device also includes an audible alerting means 9 as well as an infrared transmitter 8.

In order to use the system, the patient need only press pushbutton 3 to turn the unit on and then press pushbuttons 4 and/or 5 to operate the device in accordance with the menu presented on LCD display 2. No other controls are required on the part of the patient and the system automatically stores the test results and turns itself off if left on after a test as will be explained hereinafter.

The device according to the present invention measures the forced peak expiratory flow rate (PEFR) by converting the rate of flow of air out of the mouth into a pressure which is above ambient pressure and which is then converted to an electrical signal and processed by a microcomputer within the system. This is accomplished by blowing into measuring tube assembly 10 which comprises the smooth plain straight section of tube 11 whose inlet 12 has a diameter which is larger than outlet 13. Such a flow tube is classically known as an orifice plate flow meter.

The outlet constriction 13 is configured as a sharp edged circular opening. The resulting change in flow velocity at the outlet constriction causes a rise in the internal pressure within the tube 11 in a manner predicted by Bernoulli's equation and the equation of continuity. By measuring this internal pressure, the flow rate of the expelled air, modeled as an incompressible fluid, can be calculated using the following equation:

$$P_{(psi)} = \frac{D_{air}}{2g} Q^2 \left[ \frac{1}{A_2^2} - \frac{1}{A_1^2} \right]$$

where:

P=pressure (psi)

$D_{air}$=density of air

Q=flow (liters/minute)

g=gravity $A_1$=inlet area $A_2$=outlet area

Because of the non-uniformity of the velocity distribution and frictional effects, the actual flow rate will be less than the theoretical value given by the above equation. The theoretical flow rate is, therefore, multiplied by a correction coefficient to give the actual discharge.

The actual measurement of the flow rate depends upon the measurement of the rise in pressure above ambient atmospheric pressure within the tube 11. This is accomplished by providing a small hole 14 radially into the tube 11 and attaching a cylindrical housing 15 thereto which has a pressure sensing transducer 16 therein that converts the pressure into an electrical signal, at outputs 17 and 18, which is proportional to pressure.

The pressure sensor 16 is one of a class of transducers which convert the pressure difference across a diaphragm into an electrical output signal. The pressure difference is applied to the diaphragm via two pressure ports provided on the sensor. The system utilizes this type of differential dual port sensor in which one of the two ports is connected via tubing to sense the pressure within the flow tube and the second port is left open to sense the ambient atmospheric pressure. The resultant electrical output signals are then proportional to the difference in pressure between the inside of the flow tube 11 and the ambient atmospheric pressure inside the housing 1.

FIG. 3 shows the circuitry for processing the output from the pressure transducer 16.

In accordance with the present invention, the signals at leads 17 and 18 are fed to a differential amplifier 21 which produces two output signals at outputs 22 and 23. It should be noted that when the difference between signals 22 and 23 is obtained, any common mode noise appearing on both lines is attenuated or eliminated.

The present invention uses a second differential amplifier 24 to take into account the wide range in pressure or dynamic range which must be accommodated by the system. In this way, the system can be used to measure both low flow rates of children and severe asthmatics, as well as the high flow rates of healthy adults.

Since the pressure produced by the flow tube 11 is proportional to the square of the flow rate, the range of pressures which need to be measured is very high and extends from around 0.001 to 0.3 psi. Conventional amplification approaches would either use very high gain to sense low pressure and saturate an amplifier on high pressures, or use low gain which is low enough as to not saturate on the highest pressures but not provide enough gain to properly resolve the lowest pressures.

In the present invention, a piecewise linear amplification approach is used where the two amplifiers 21 and 24 are used simultaneously and both outputs are used. The differential amplifier 21 is the low gain amplifier which produces low gain signals at 22 and 23, whereas the differential amplifier 24 is the amplifier and produces high gain outputs at 25 and 26.

These outputs are converted to digital data by an analog to digital converter 28 which is part of a microprocessor circuit 20. The A/D converter 28 is fed via a multiplexer 27 which is capable of receiving multiple outputs and which is controlled by processor 29 to select one input to the multiplexer at a time and apply it to the A/D converter 28 for conversion into digital data.

The analog to digital converter 28 converts the amplified transducer voltage from the differential amplifiers 21 and 24 and the processor then determines which of the two amplifier circuits should be used. If the high gain signal 25, 26 is near or at saturation, the low gain signal 22, 23 is used and the high gain signal is ignored. Conversely, if the high gain signal is sufficiently below its saturation level, it is used and the low gain signal is ignored.

The present invention also utilizes the multiplexed A/D converter to further advantage by allowing each of the two differential outputs of each amplifier stage to be separately converted without the need for an additional differential amplifier to obtain a single ended conversion. In other words, each amplifier output consists of two differential signals which are then subtracted in their digital formats to yield a final usable value of the transducer pressure.

As shown in the above equation, since the flow rate through the tube 11 is proportional to the square root of the pressure, it is thus proportional to the square root of the electrical output signal from the pressure transducer. The processor 29 processes this number by converting it to its square root and multiplying it by a predetermined constant yielding the flow rate within the tube.

The microprocessor 20 monitors the calculated flow rate values to detect the beginning of a test. The flow rate is zero (0) until the patient begins a test by blowing into the flow tube 11. When the flow rate values increase beyond the predetermined threshold, the flow rate values are stored in the memory 30 at a predetermined rate until the flow rate decreases below a threshold or a predetermined time has elapsed. This indicates that the test is complete and the microprocessor processes the flow rate values stored in memory to find the peak value.

The peak value can be determined by a number of algorithms depending on how much accuracy and noise suppression is required. One algorithm is to use the highest value stored in memory. Others include complex signal processing algorithms such as curve fitting which find the closest mathematical formula that matches the stored data. Once the peak value is determined, it is converted into a format which can be displayed to the user of the device on the LCD display 2 which is controlled by the processor 29.

The differential amplifier 21 preferably amplifies the pressure signal by a gain of 1,000 and these signals are further amplified by a gain of 6 by differential amplifier 24 to produce the high gain signal.

As noted above, the A/D converter 28 samples the two differential voltages representing the applied pressure signal under the control of the processor 29. When the processor detects that the high gain differential amplifier 24 has exceeded a predetermined threshold, both high gain and low gain samples are stored in RAM 30. After a predetermined time or when the signal falls below a predetermined value, new values are no longer stored and the processor sorts through the stored values to find the peak value of the pressure signal. Since both high gain and low gain signals are stored for each sample interval, the processor 29 also checks whether the high gain signal has exceeded a saturation level. If the high gain signal has reached saturation, the low gain signal is used instead. This provides the high resolution for low level signals produced by children and asthma sufferers, while simultaneously making available higher amplitude signals from healthy adults. Storing both high gain and low gain signals simultaneously, maximizes the dynamic range of the system.

The power supply 32 has its output fed to a reference voltage circuit 33 which provides a reference for the A/D converter 28. Since both the transducer signal and the reference voltage is proportional to the analog voltage supply of power supply 32, any changes in the supply voltage appear as a common mode signal to the A/D converter and are eliminated. The multiplexer 27 also has the output of the voltage supply 32 divided through divider 34 and fed to one of the inputs of the multiplexer so that it can be monitored to allow the processor 29 to detect a low battery condition and inform the user via the LCD display 2.

The system also includes a temperature sensor 31 whose output is also fed as an input to multiplexer 27 and allows the processor 29 to determine if the operating temperature is within allowable limits or to scale the readings appropriately for changes in operating temperature.

Clock circuit 35 is real time clock and provides clock signals to all of the components in the system. The system also includes a wake-up alarm 36 which is fed by the clock circuit. The clock circuit 35 provides time and date tags for the peak flow data stored in the RAM 30.

The wake-up alarm 36 receives the clock output to keep track of the preprogrammed times that the system must automatically turn on to prompt the user either to take medication or to perform tests. The alarm circuit 36 initiates a power on cycle for the microprocessor 20 upon the occurrence of a preprogrammed automatic turn on time.

Figure 5:
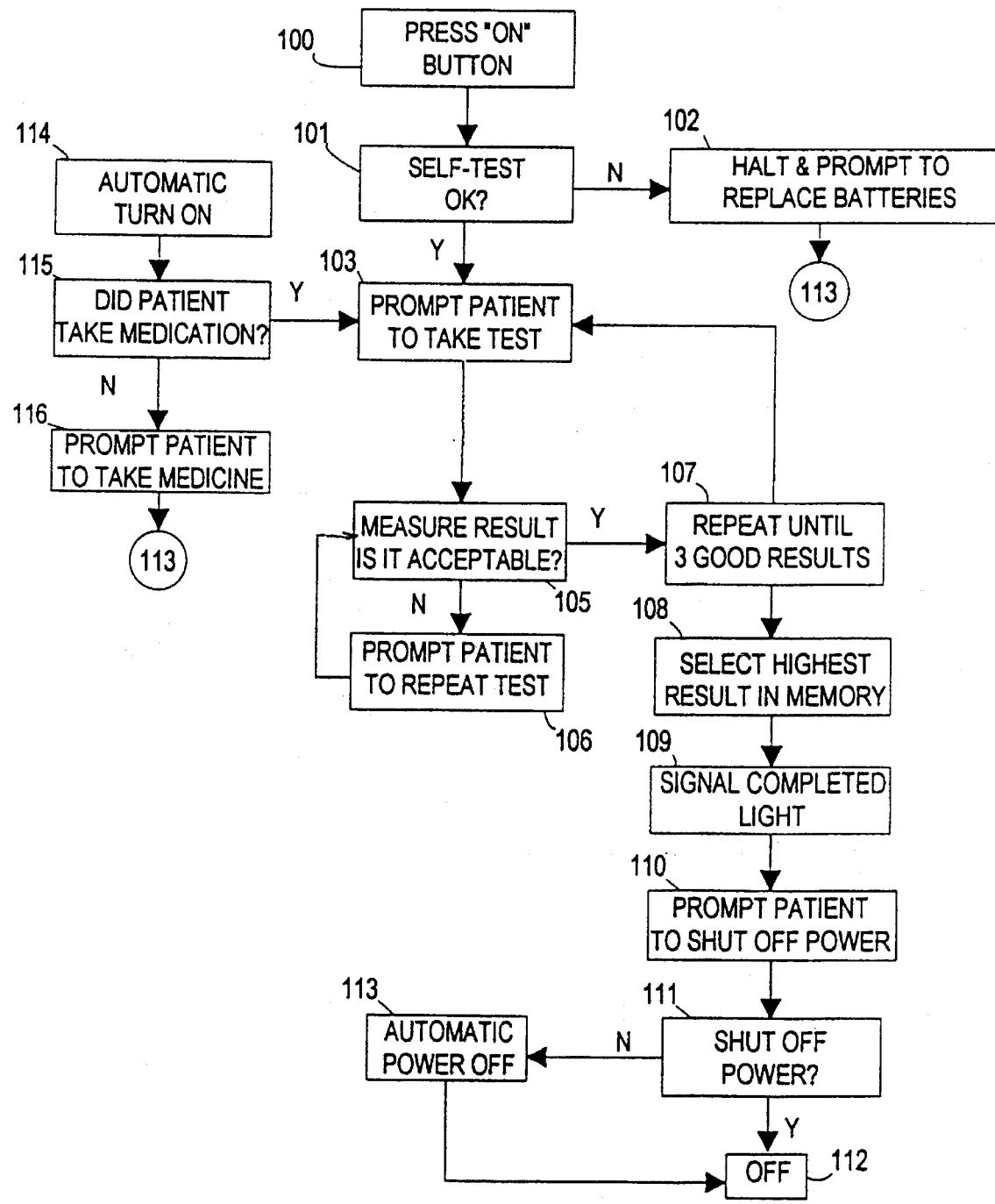
FIG. 5 is a flow chart of the method of the present invention carried out by the device of FIG. 1.

The method of use of the system is shown in the flow diagram of FIG. 5. To begin using the system, in step 100 the patient presses on button 3 and the system goes through a self test in step 101. If the self test is unsuccessful, the system will prompt the user in step 102 to change the system batteries of power supply 32, or signal the operator that the device should be returned to the factory (if the self-diagnostic test fails), and will thereafter automatically turn off.

If on the other hand the self test is successful, the LCD display 2 will visually confirm by indicating to the user that the self test and batteries are O.K. and this will be followed by an audible beep signal at audio output 9 and a visual display at step 103 prompting the patient to take a test by blowing hard into the measuring tube assembly 10.

After blowing into the tube, the system will, optionally, measure the signal to see if it is acceptable in step 105. If the result is acceptable, the patient will again be prompted to take the test by the LCD display 2. The successful measurements are repeated until three good results are obtained as noted in step 107. If on the other hand the system measures the signals and finds they are erroneous for whatever reason, in step 106 the patient will be prompted to repeat the test.

After the three good results are obtained, the processor 29 in step 108 proceses the biological data stored in memory and indicates that the test has been completed by turning on the respective signal light 7a, 7b or 7c. To calculate the forced peak expiratory flow of air (PEFR), the processor simply selects the highest signal (which represents the flow rate); to calculate the forced expiratory volume in the first second (FEV. 1), the processor integrates the flow rate signal over the first second; and to calculate the forced vital capacity (FVC) the processor integrates the flow rate over the entire patient blow period.

The light 7a is green, indicating that the patient is "OK". The light 7b is yellow, indicating that the patient should exercise "caution", and the light 7c is red, indicating that the patient has failed the test and should consult a doctor. The system can also display the result on the LCD display to show the user the actual measured value of PEFR, FEV. 1 and/or FVC. If the user does not shut off power in step 111, the system will automatically shut power off in step 113 and lead to the final system off in step 112.

The system also has the wake-up alarm 36 which automatically turns the system on in step 114. If so programmed, the system can first prompt the patient to find out if the patient took medicine. If not, in step 116 it can prompt the patient to take medicine and proceed to automatic power off. If the patient has taken the medicine, the system will then proceed to the routine starting in step 103 wherein a test is performed.

The system, by its design, enables the physician to customize the operation and options for the patient through the self prompting LCD display 2. To program the unit, the physician depresses the two right buttons 4 and 5 simultaneously for five seconds during start-up. The physician is then permitted to set a number of programming modes, four of which are as follows:

A "time" mode allows the physician to set the time and date for the device.

An "alarm" mode allows a reminder alarm to be turned on or off and to set the alarm times for up to six different time settings.

A "normal" mode allows the setting of the expected normal test results for patient comparison and the setting of accepted variations for notation to the doctor.

The instrument also has a "reading" mode to allow the doctor to either erase the patient test log and/or alarm settings, or to view through the display all of the recorded data.

The system further provides a "lockout" mode in which the physician can limit the time in which a patient may use the monitor from 15 days to 6 months before the unit will start flashing, at power on, a message to return to the doctor. The unit will become inoperative when the time period elapses until rest by a physician.

When the unit is turned on by pressing the on button 3, the green LED light 7a is flashed and one beep is sounded and the green ready light 6a is lit. If no button is pressed thereafter, the unit will automatically turn off after two minutes.

The power supply 32 preferably comprises a replaceable battery with a backup lithium battery.

As a result of the above-mentioned programming capability, the system is able to alert the patient that it is time for a test by means of audible alarm 9. The system then prompts the patient on liquid crystal display 2 to blow into the measuring tube three times, or any other recommended number of repetitions, and it automatically records the highest reading of peak flow rate along with the date and time of the test. Before automatically shutting down, the system can remind the patient on display 2 to take the prescribed medication and displays the dosages thereof, as has been preprogrammed by the doctor. After shutting down, an internal clock of the system will cause it to alert the patient with audible alarm 9 after a predetermined time. It can then either manually or automatically query the patient on display 2 whether the medication was taken before proceeding to the next peak flow rate test. When the patient acknowledges that the prescribed medication was taken by pressing button 5, the dosage is recorded along with the peak flow rate reading of the next test. If the patient indicates that the medicine was not taken by pressing button 4, the system again displays the correct dosages on display 2 and initiates another alarm ten minutes later. If no medicine was taken the second time, a zero dose is recorded and the unit shuts down until the next program testing time.

The system is capable of being used for peak flow rate testing at any time by the patient by operating controls 3–5 on the outside of the housing. Thus the user can press on button 3 and follow prompts on display 2 for a patient initiated test. Upon completion of any flow test, the unit displays the actual peak flow as well as the normal value for that patient as programmed by the doctor. The unit can then indicate on lights 7a–7c whether the results were within the normal range, in a cautionary range below normal or well below the normal range warranting consultation with the doctor. These ranges can be preset by the doctor and the indications of the ranges can be made by use of a green light 7a indicating normal range, a yellow light 7b indicating caution and a red light 7c indicating sufficiently below normal to warrant calling a doctor. The ranges can be preprogrammed by the doctor for the particular patient.

The system also enables the doctor to program the maximum number of days to be used before the patient should return. Thus, for example, within five days of the return date, each time the unit is turned on manually or by a preset alarm, a message is displayed on display 2 prompting the patient to return to the doctor before allowing a test to be run and recorded. After the date for return, tests would no longer be able to be run and only the prompt is displayed. A suitable alarm can be emitted from the device after a given amount of time past the return date, for example ten days to indicate that the device has been stolen.

FIG. 6 shows how the system is used in a physician's office to download the stored biological data and time data into the physician's personal computer for subsequent analysis and printing. The PEFR device 1 is placed on an interface unit 120 which, in turn, is connected to a personal computer via a conventional RS-232 connector. The interface unit 120 contains an infrared receptor 122 which receives the data transmitted from the device 1 via the IR transmitter 8.

The PEFR device 1 is set for transmission by pressing the buttons 4 and 5 simultaneously for five seconds during the initial self test of this device and then following the menu that appears on the LCD display 2.

The personal computer 124 uses data management software which receives the data supplied at the internal RS-232 circuit board, stores the data in memory and displays it on the computer screen. If desired by the physician, this data may be printed in raw data or graphic form by the computer printer 126.

Figure 8:
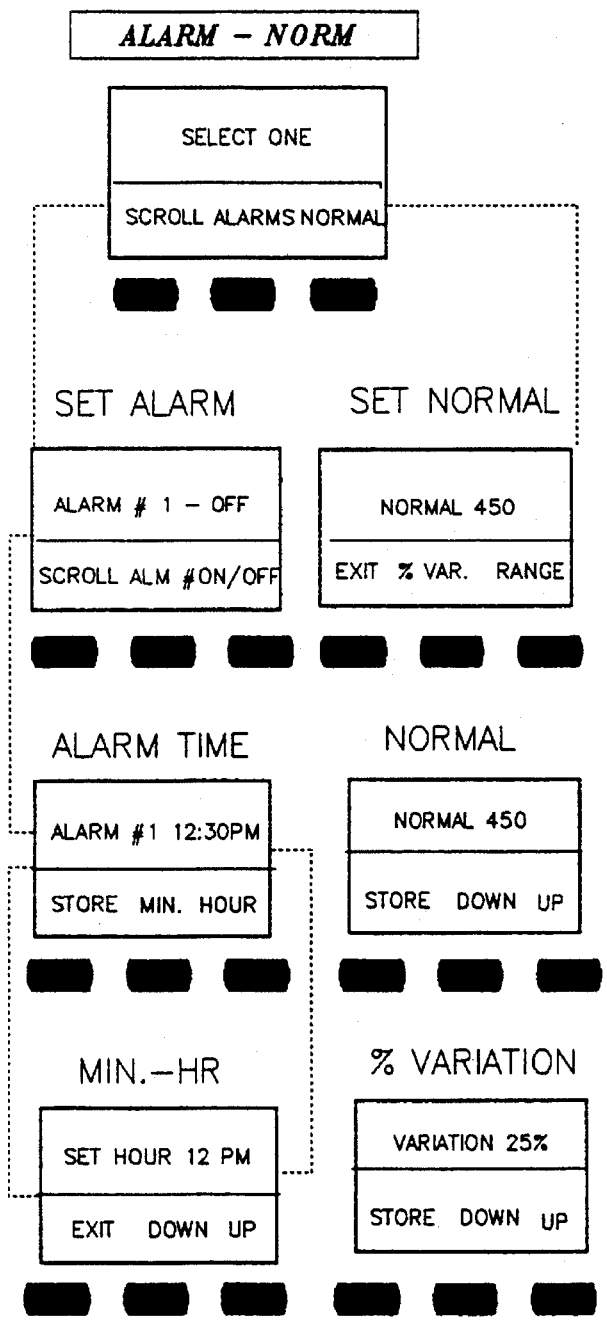
FIG. 8 is a diagram illustrating the physician programming menu for setting the patient prompter alarms.
Figure 9:
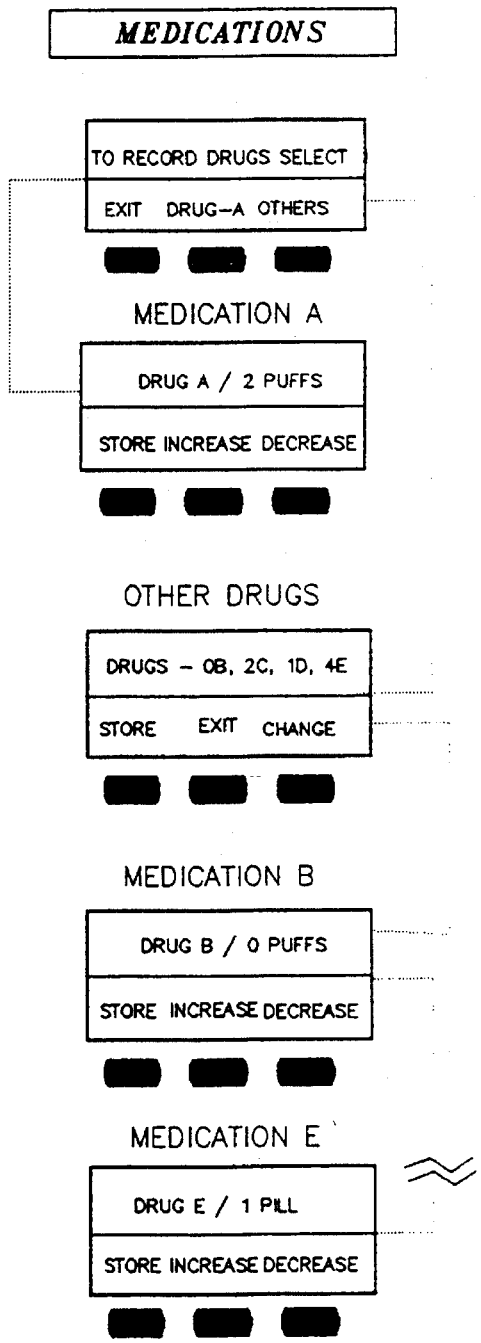
FIG. 9 is a patient menu, allowing the patient to record medication.

FIGS. 7–9 illustrate three types of menus which are imaged on the LCD display 2 of the PEFR device 1. The first menu, called "factory-lock", is illustrated in FIG. 7 This menu facilitates either calibration of the device or lock-out to prevent the unit from operating after a certain period (for example if a patient fails to return the unit to the physician for data read-out).

The calibration function may be selected at any time to recalibrate the device. Initial calibration is performed at the factory but this calibration can easily be adjusted in the field using the factory-lock menu.

During calibration, a pneumo-tachometer is placed with its mouthpiece in series with the measuring tube 10 so that all of the air leaving the pneumo-tachometer enters the measuring tube opening 12. Alternatively, the output of a calibrated syringe can be supplied directly to the opening 12 of the tube 10. One or more readings are then taken by the PEFR device 1 and the calibration reference. The average of these readings is then taken and the calibration of the device 1 is adjusted to that of the reference using the following steps:

1. The device 1 is turned on by pressing the on/off button 3.
2. When the "SELF TEST—WAIT" message is displayed on the LCD display 2, the buttons 4 and 5 are simultaneously pressed.
3. When the display reads "SCROLL—ENGLISH—SPANISH" the SCROLL button is pressed 5 times until "EXIT—FACTORY—LOCK" is displayed.
4. The FACTORY button is then pressed. A SOURCE value and a METER value are displayed on the top line. Using the DECREASE or the INCREASE buttons, the METER value is adjusted until it matches the average device 1 readings rounded to the nearest 10 lpm.
5. While simultaneously pressing the RECORD MEDICATION button, the INCREASE or DECREASE buttons are pressed to adjust the SOURCE value until it matches the average reference reading rounded to the nearest 10 lpm.
6. When the SOURCE and METER reading agree with the reference and device 1 averages respectively, the EXIT button is pressed to lock in the calibration. This calibration is permanently recorded in the device 1 memory until it is changed by repeating steps 1 through 6 above.

The lock-out feature prevents the device 1 from being operated after a selected number of days has passed. After this time, the device 1 will not operate except to display the message: "LOCK-OUT CONDITION EXISTS RETURN TO DOCTOR NOW".

To set the number of "days" before the lock-out message is displayed, the days button is pressed. The display shows the current time period, which can be increased or decreased by multiple depressions of buttons 4 and 5 and then stored by pressing button 3.

To reset the unit when the lock-out message is displayed, the buttons 4 and 5 are pressed together to advance to the lock window. The button 4 is then pressed to turn the lock off and exit to the main opening window. Thereafter, the button 3 is pressed to exit the lock program.

The "alarm-normal" menu is illustrated in FIG. 8. To leave or skip this program, the scroll button is pressed. The "alarm" button is pressed to set the alarm which brings up the menu on the left side of FIG. 8. Pressing the button "normal" brings up the normal menu on the right side of FIG. 8. These functions are the percent variation—the minimum acceptable percentage—of deviation from the normal expected score on the "consult doctor" light 7c. The default setting for this light is 50% of normal. Pressing the range button sets the normal expected score. The range is from 100 to 700 l/min. Pressing the store button sets the variation percent and/or the normal expected score.

Similarly, the alarm time in hours and minutes each day may be changed and set by pressing the "store" button.

The "medication" menu as shown in FIG. 9 is called up by pressing the "record medication" button 6 on the device. The first window to appear after pressing this button will allow the patient to choose between entering data on drug A only and returning to the opening menu, or all drugs B through E. If drug A (only) is selected, the dose is set by pressing the "increase" or "decrease" buttons and then the "store" button, which returns the device to the opening menu.

If "all drugs" is selected, the unit will advance from drug B through drug E. If no dose for B drug was taken, the "store" button with zero dose is displayed. The display always beings with the last dose used for each drug.

All dose increments are in number of puffs for drugs A, B and C. Drugs D and E are in pills (one half increments).

After drug E has been recorded or skipped, the program automatically returns to the opening menu. Optionally, to review the medication log, the "medication" and the "review" buttons are pressed simultaneously at the opening menu.

Figure 10:
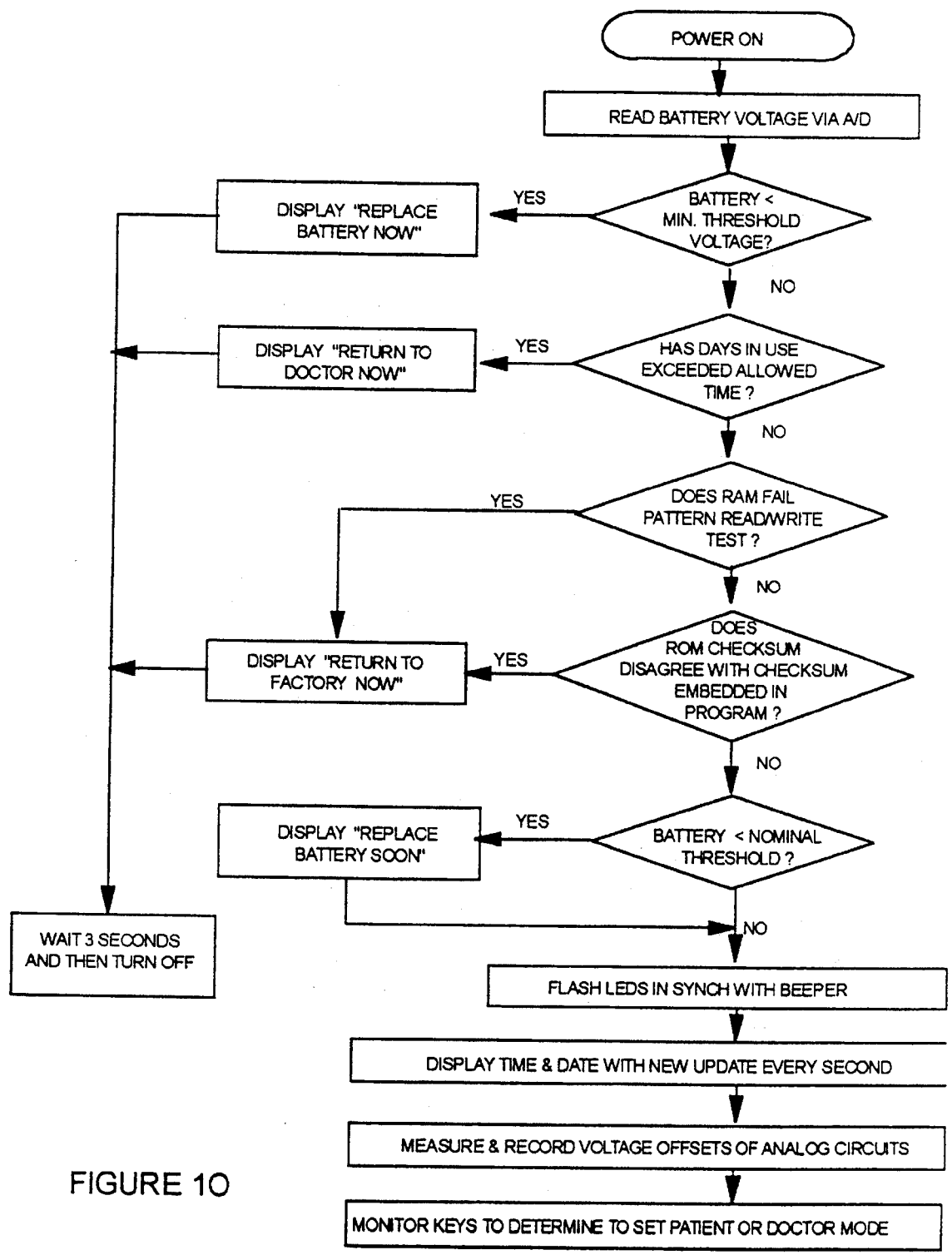
FIG. 10 is a flow chart of the "Power-On" diagnostic software module within the device of FIG. 1.

The software programs stored in the device are organized into modules: The "power on and diagnostic module" (FIG. 10); "the data record generation and storage module" (FIG. 11); the "peak pulse detection and data management module" (FIG. 12) and the "data transmit module" (FIG. 13). The flow charts of FIGS. 10–13 are self-explanatory and require only a few general comments.

The self-test of the device (FIG. 10) is effected by adding all bits in ROM together and comparing this "check sum" (or, more particularly, the last two digits thereof) with the expected check sum stored in the program.

Figure 11:
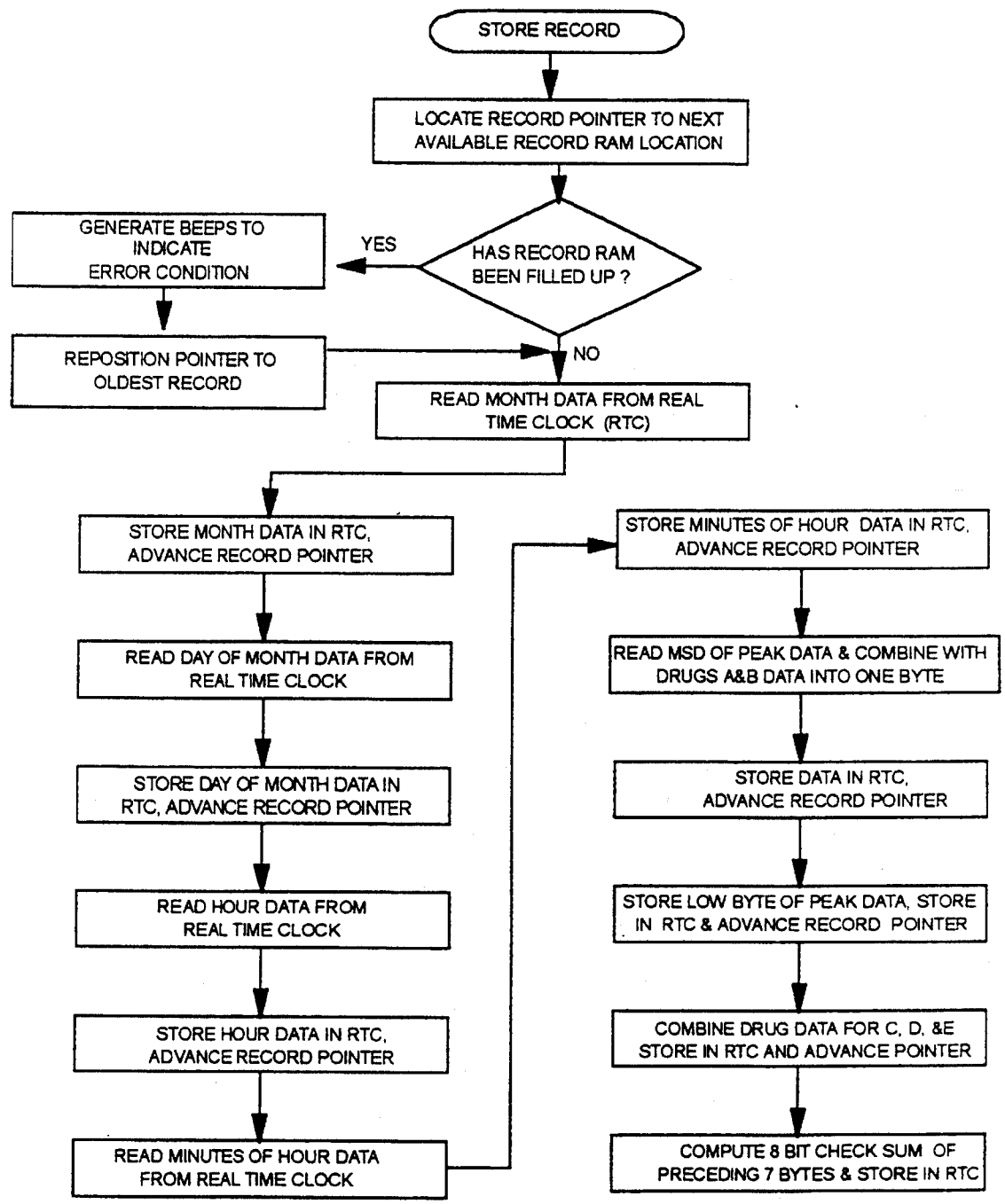
FIG. 11 is a flow chart of the data record generation and storage software module.

In FIG. 11, the real time cock (RTC) contains a battery backed RAM for maintaining the month, day, hour and minutes. This current time is stored in the non-volatile memory of the device 1 together with the PEFR data obtained from the patient.

Figure 12A:
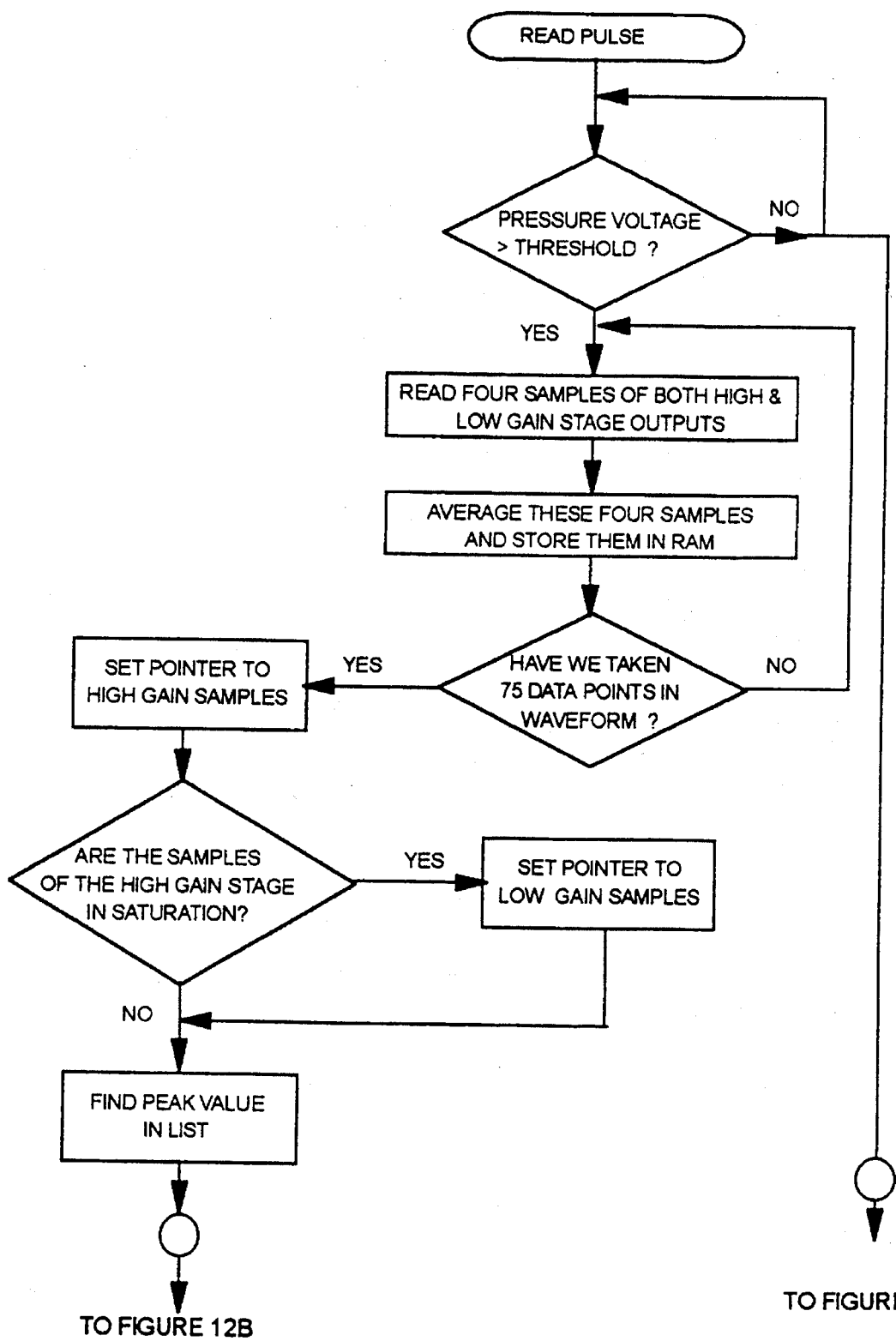
FIG. 12 is a flow chart of the peak pulse detection and data management software module.
Figure 12B:
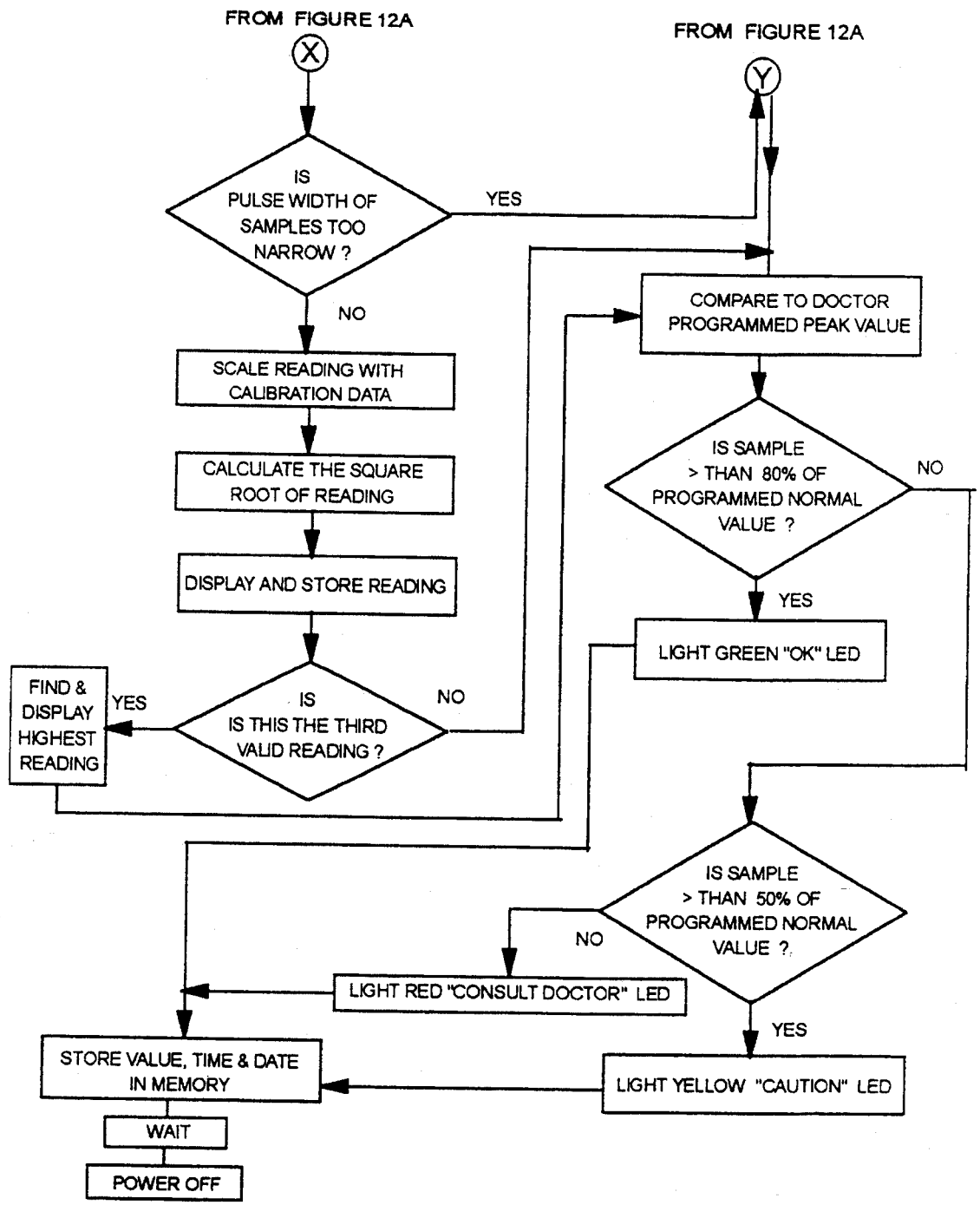
Figure 13:
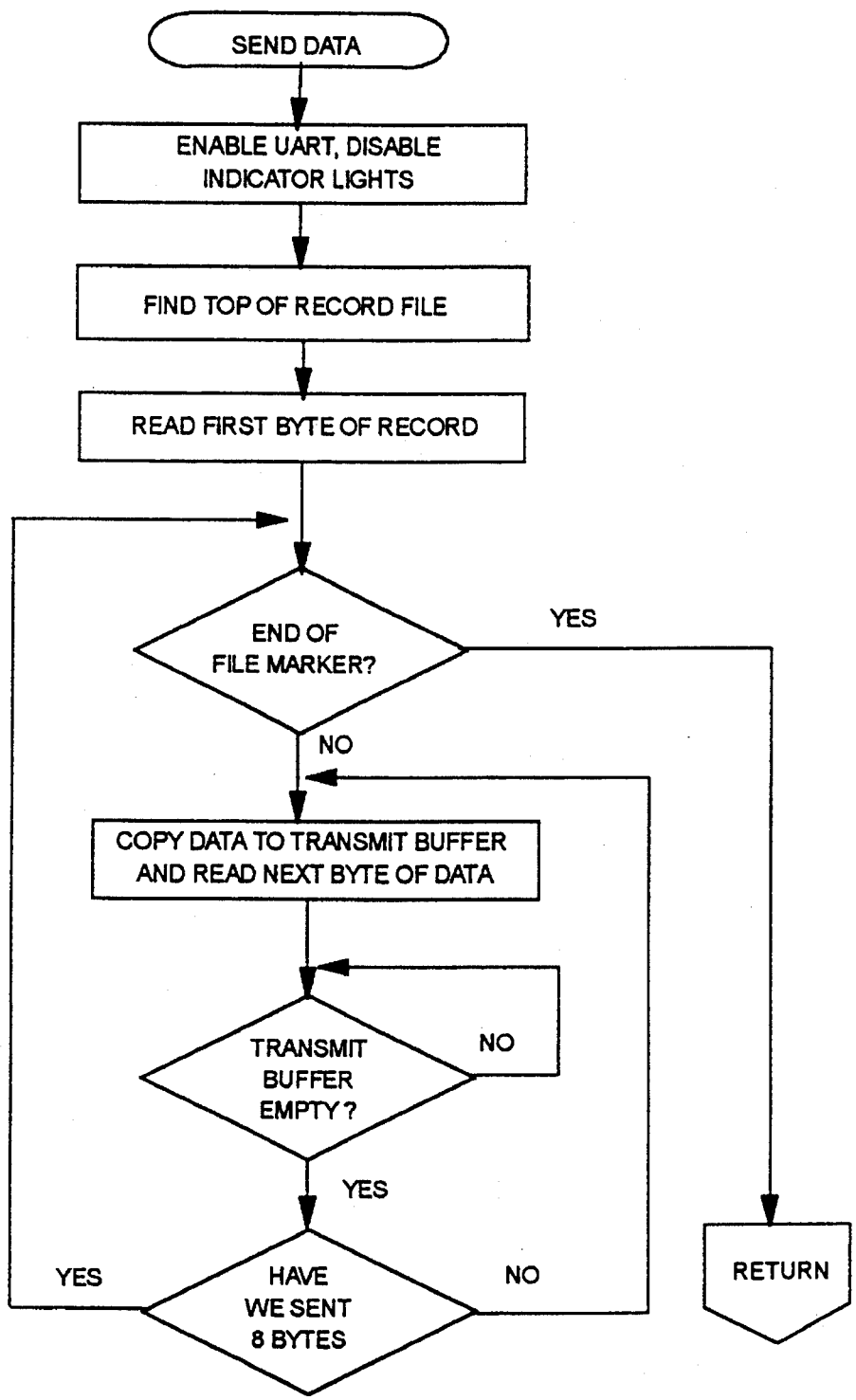
FIG. 13 is a flow chart of the data transmission software module.

FIG. 12 shows how the digital samples of the analog pressure data are processed. Only samples which are above a given threshold are accepted and stored. To ensure that the sample data is not spurious, a wave form must be formed of at least 75 consecutive pulses before it will be considered valid and analyzed to determine the peak value. Once the peak is found, it is scaled with the calibration data, stored in the non-volatile memory and compared with the "normal" value to determine which of the lights 7a, 7b and 7c should be illuminated.

Finally, FIG. 13 illustrates a standard routine for transferring data from the non-volatile memory to a transmit buffer. The data contained in this buffer is transmitted in serial form by the infrared transmission link or optionally transmitted by cable from an RS-232 serial port connector on the unit.

It is understood that the embodiments described hereinabove are merely illustrative and are not intended to limit the scope of the invention. It is realized that various changes, alterations, rearrangements and modifications can be made by those skilled in the art without substantially departing from the spirit and scope of the present invention.

What is claimed is:

1. A patient-operated device for testing and recording the respiratory status of a patient, said device comprising;
   a) a portable housing;
   b) prompter means in the housing for prompting the patient to operate the device;
   c) sensor means affixed to the housing for sensing an expiratory flow rate of air of the patient and for generating a first signal representative of said flow rate of air;
   d) processor means in the housing for processing said first signal to generate biological data representative of at least one of the values in the group consisting of peak expiratory flow rate (PEFR), forced expiratory volume in the first second (FEV. 1) and force vital capacity (FVC) of the patient;
   e) time-generating means in the housing for generating time data representative of a time when said flow rate of air was sensed;
   f) storage means in the housing for storing the biological data produced by said processor means and the time data produced by said time-generating means; and
   g) retrieval means in the housing for retrieving from said storage means the biological data together with the time data.

2. The device according to claim 1, wherein the prompter means comprises wake-up alarm means responsive to the time-generating means for prompting the patient to cause the sensor means to sense said flow rate of air after a preselected time interval from a previous time when said flow rate of air was sensed.

3. The device according to claim 2, wherein the prompter means comprises means for producing an audible alarm.

4. The device according to claim 1, wherein the prompter means comprises display means for indicating when the patient is to blow air into the device.

5. The device according to claim 1, wherein said processor means is further operative to analyze said biological data to provide a test result and wherein said device further comprises means for indicating to the patient the test result.

6. The device according to claim 5, wherein said indicating means indicates to the patient whether the test result is above or below a normal predicted value.

7. The device according to claim 5, wherein said indicating means include a red, a yellow and a green color and means for indicating one of said colors in response to the test result.

8. The device according to claim 7, wherein said indicating means is operative to indicate said green color when the test result is greater than 80% of a normal predicted value.

9. The device according to claim 7, wherein said indicating means is operative to indicate said red color when the test result is less than 50% of a normal predicted value.

10. The device according to claim 7, wherein said indicating means is operative to indicate said yellow color when the test result is between 50% and 80% of a normal predicted value.

11. The device according to claim 5, wherein the means for indicating the test result comprises light emitting diodes which, when illuminated, indicate whether the test result was positive or negative.

12. The device according to claim 1, wherein the sensor means comprises an air flow tube having an air flow inlet, an air flow outlet and transducer means for sensing said flow rate of air through said tube.

13. The device according to claim 12, wherein the transducer means comprises a pressure transducer in fluid communication with the flow tube via an opening in the flow tube between said inlet and outlet and in communication with ambient pressure, said pressure transducer producing said first signal in response to the difference between the pressure at said opening in said flow tube and ambient pressure.

14. The device according to claim 13, wherein said opening in said flow tube extends substantially radially through a wall of said tube.

15. The device according to claim 12, wherein said outlet in the flow tube has a smaller cross sectional area than said inlet.

16. The device according to claim 15, wherein said tube is substantially cylindrical in shape.

17. The device according to claim 12, wherein said tube is removably attached to the housing.

18. The device according to claim 1, wherein said processor means includes software means for selecting a peak value of the flow rate of air sensed by said sensor means.

19. The device according to claim 18, wherein said software means includes means for rejecting the peak value when it falls below a prescribed threshold.

20. The device according to claim 19, wherein said software means includes means for rejecting the peak value of air flow rate when the air flow rate does not remain above said prescribed threshold for a prescribed period of time.

21. The device according to claim 18, wherein said software means includes means for compensating the peak value in dependence upon temperature.

22. The device according to claim 1, wherein said retrieval means includes a transmission link for connection between said device and a host computer for downloading said biological and time data to said host computer.

23. The device according to claim 22, wherein said transmission link includes infrared transmitter means in said housing for transmitting a data signal to an infrared receiver means, separate from said housing and connected to said host computer, for receiving said data signal and forwarding the same to the host computer.

24. The device according to claim 1, further comprising at least three pushbuttons on said housing, each pushbutton being connected to respective means for implementing at least one function for operating the device.

25. The device according to claim 24, wherein one pushbutton and its respective implementing means are operative to switch the device on and off.

26. The device according to claim 24, wherein the prompter means comprises display means for indicating an operating menu and wherein at least two of said pushbuttons and their respective implementing means are operative to select functions from the menu.

27. The device according to claim 24, wherein said processor means includes software means for selecting between an operating mode for a patient and a programming mode for a physician, and wherein two of said pushbuttons and their respective implementing means are operative to select the programming mode when both buttons are pressed simultaneously for a prescribed period of time, thereby preventing unauthorized or inadvertent access to the physician's programming modes.

28. The device according to claim 24, wherein said processor means includes software means for calibrating the device, said calibrating means including means for displaying a measured flow rate of a known rate of air flow, and means responsive to at least one of said pushbuttons for changing the measured flow rate to match the known flow rate.

29. The device according to claim 1, wherein the prompter means comprises display means for displaying at least one of the type and dosage of medication to be taken by the patient.

30. The device according to claim 29, further comprising means, responsive to actuation by a human operator, for changing at least one of the type, dosage and time of the medication to be taken by the patient.

31. The device according to claim 1, wherein said prompter means further comprises wake-up alarm means responsive to the time-generating means for prompting the patient to take prescribed medication.

32. The device according to claim 1, further comprising key entry means for manually logging into said storage means the type of medication taken by the patient, and wherein said time-generating means further enters into the storage means the time that the medication was taken.

33. The device according to claim 1, further comprising means for clearing the data stored in said storage means, said clearing means including security means for preventing unauthorized operation.

34. The device according to claim 1, wherein the processor means comprises a first amplifying means for amplifying said first signal to produce a low gain signal, second amplifying means for amplifying the low gain signal to produce a high gain signal and means for selecting between the high gain and low gain signals to generate biological data.

35. The device according to claim 1, wherein the retrieval means comprises a non-volatile random access memory.

36. The device according to claim 1, wherein the processor means has means for automatically turning the device off after a predetermined time interval.

37. The device according to claim 1, wherein said processor means is operative to process said first signal to generate biological data representative of forced expiratory volume in the first second (FEV. 1).

38. The device according to claim 1, wherein said processor means is operative to process said first signal to generate biological data representative of forced vital capacity (FVC).

39. The device according to claim 1, wherein said processor means is operative to process said first signal to generate biological data representative of peak expiratory flow rate (PEFR).

40. A method for testing and recording the respiratory status of a patient, said method comprising the steps of;

a) prompting the patient to cause the testing of a expiratory flow rate of air;

b) sensing the expiratory flow rate of air of the patient and generating at first signal representative of said flow rate of air;

c) processing said first signal to generate biological data representative of at least one of the values in the group consisting of peak expiratory flow rate (PEFR), forced expiratory volume in the first second (FEV. 1) and forced vital capacity (FVC) of the patient;

d) generating time data representative of a time when said flow rate of air was sensed;

e) storing the biological data and the time data; and f) retrieving the stored biological data together with the time data.

41. The method according to claim 40, wherein the step of prompting comprises prompting the patient to permit the sensing of said flow rate of air after a preselected time interval from a previous time when said flow rate of air was sensed.

42. The method according to claim 41, wherein the step of prompting comprises producing an audible alarm.

43. The method according to claim 40, wherein the step of prompting comprises displaying patient instructions on a liquid crystal display.

44. The method according to claim 40, further comprising the steps of analyzing said biological data to provide a test result and indicating to the patient the test result.

45. The method according to claim 44, wherein said indicating step includes indicating to the patient whether the test result is above or below a normal predicted value.

46. The method according to claim 44, wherein said indicating step includes the step of indicating one of a red, yellow and green color in response to the test result.

47. The method according to claim 46, wherein said indicating step includes the step of indicating said green color when the test result is greater than 80% of a normal predicted value.

48. The method according to claim 46, wherein said indicating step includes the step of indicating said red color when the test result is less than 50% of a normal predicted value.

49. The method according to claim 46, wherein said indicating step includes the step of indicating said yellow color when the test result is between 50% and 80% of a normal predicted value.

50. The method according to claim 40, wherein the processing step includes the step of processing said first signal to generate biological data representative of the forced expiratory volume in the first second (FEV. 1).

51. The method according to claim 40, wherein said processing step includes the step of processing said first signal to generate biological data representative of forced vital capacity (FVC).

52. The method according to claim 40, wherein said retrieving step includes the step of downloading the stored biological data and time data into a host computer.

53. The method according to claim 40, wherein said processing step includes the step of processing said first signal to generate biological data representative of peak expiratory flow rate.

54. In a device for monitoring a biological condition of a patient having sensor means for sensing the biological condition of the patient and for generating a signal representative of the biological condition and processor means for processing said signal to generate biological data representative of the biological condition, the improvement wherein said processor means comprises first amplifying means for amplifying the signal to produce a low gain signal, second amplifying means for amplifying the low gain signal to produce a high gain signal and means for selecting between the high gain and low gain signals to generate the biological data.

55. In a method for monitoring a biological condition of a patient, including sensing the biological condition of the patient and generating a signal representative of the biological condition and processing said signal to generate biological data representative of the biological condition, the improvement wherein the step of processing comprises first amplifying the signal to produce a low gain signal, thereafter amplifying the low gain signal to produce a high gain signal and selecting between the high gain and low gain signals to generate the biological data.

\* \* \* \* \*